United States Patent [19]

Song

[11] Patent Number: 4,915,909

[45] Date of Patent: Apr. 10, 1990

[54] METHOD OF CONTROLLING ALGAE GROWTH

[75] Inventor: Peter Song, Midlothian, Ill.

[73] Assignee: Nalco Chemical Company, Naperville, Ill.

[21] Appl. No.: 254,247

[22] Filed: Oct. 5, 1988

[51] Int. Cl.$^4$ ............................................. A01N 25/02
[52] U.S. Cl. .................................... 422/28; 106/15.05; 106/18.32; 422/6; 422/32; 422/37; 422/40; 427/331; 427/336; 427/397
[58] Field of Search ................... 422/6, 28, 32, 37, 40; 427/331, 336, 397; 106/15.05, 18.32

[56] References Cited

U.S. PATENT DOCUMENTS

| | | | |
|---|---|---|---|
| 3,342,629 | 9/1967 | Martin | 422/40 X |
| 3,949,086 | 4/1976 | Wolfson | 514/515 |
| 3,967,011 | 6/1976 | Dunn, Jr. et al. | 427/397 X |
| 4,297,258 | 10/1981 | Long, Jr. | 524/200 |
| 4,323,602 | 4/1982 | Parker | 424/81 X |
| 4,806,263 | 2/1989 | Leathers et al. | 134/42 X |

FOREIGN PATENT DOCUMENTS 2138292 10/1984 United Kingdom .

OTHER PUBLICATIONS

"IPBC-A NEW FUNGICIDE FOR WOOD PROTECTION", Reprint from Modern Paint and Coatings, Nov. 1984, Hansen.
TROYSAN POLYPHASE P100 Technical Data Sheet, Jun. 1985, Troy Chemical Corporation.

*Primary Examiner*—Barry S. Richman
*Assistant Examiner*—Timothy M. McMahon
*Attorney, Agent, or Firm*—Joan I. Norek; John G. Premo; Donald G. Epple

[57] ABSTRACT

The growth of algae and algae-like microorganisms on wood surfaces normally in contact with an aqueous system's water may be controlled by applying to the wood a solution of a certain biocidal agent and then flooding the wood with sufficient water to exceed the solubility limit of such agent in the solvent used.

12 Claims, No Drawings

METHOD OF CONTROLLING ALGAE GROWTH

TECHNICAL FIELD OF THE INVENTION

The present invention is in the technical field of algae growth control, and in particular the control of algae growth to prevent fouling of aqueous systems.

BACKGROUND OF THE INVENTION

Fouling of water-using, or aqueous, processes and systems, particularly industrial aqueous systems, is an extremely serious problem. Fouling results from the settling out of suspended solids, build up of corrosion products, and growth of microbial masses. Fouling interferes with heat transfer, reduces the water flow, and also promotes severe corrosion under the deposits. Microbial deposits in an aqueous system often require treatment with both a biocide and a dispersant to remove such deposits from surfaces. Among the problematic microbial organisms are algae, which, since they generally require sunlight to grow, are found on open, exposed areas, such as cooling tower decks. Most algae grow in dense, fibrous mats that plug distribution piping and flumes, and portions of such mats break off and deposit at other locations in the system. Algae also are a nutrient for other undesirable organisms and algae mats provide areas for subsequent growth of anaerobic bacteria.

For industrial aqueous systems, control of microbial growth by heat or radiation is generally impractical and bulk water treatment with nonoxidizing biocides is often prohibitively expensive and environmentally unsuitable. Thus chemicals that in water provide hypochlorous and hypochlorite ions, for instance chlorine, are often the bulk water treatment of choice.

In recirculating cooling towers, algae growth on the open decks present a serious problem. Large volumes of water are employed in such systems, and the water generally has a relatively short half-life in the system, and thus treatment of the bulk water with even 100 ppm of chemical biocide requires a great amount of biocide. Further, in some recirculating cooling towers the treatment of the bulk water with an oxidizing biocide such as chlorine has little to no effect with respect to algae growth on the cooling tower deck. If the algae growth on the deck becomes heavy, portions of even killed algae mats may break off and foul the heat exchanger. In practice cooling tower decks generally need to be cleaned or scrubbed to remove unacceptable levels of algae periodically, which requires the tower to be shut down, adding greatly to the overall cost of operations. Typically a cooling tower will be shut down for algae removal from the deck several times a season, and some towers require such deck cleaning several times a month.

It would be desirable to provide a method of controlling algae growth at the site of the open decks of recirculating cooling towers, or similarly situated areas in other aqueous systems, that is more cost effective than present bulk water treatments, including bulk water treatment with chlorine. It would be desirable to provide such a method that avoids bulk water treatment, and concommitant problems that often arise by the addition of chemical components to the bulk water, while effectively controlling the algae growth on the decks. It would be desirable to provide such a method that has a high degree of effectiveness and thus minimizes the frequency of deck scrubbing to remove algae growth. It is an object of the present invention to provide a method that has the above enumerated advantages and other advantages as described in more detail below.

DISCLOSURE OF THE INVENTION

The present invention provides a method of controlling the growth of algae and algae-like microorganisms on a surface of wood that is normally in contact with the water of an aqueous system, which method comprises the steps of first applying to the wood surface a certain type of biocide, described below, in a solvent or solvent system that includes a water-miscible organic solvent, and then flooding the wood surface so treated with sufficient water so as to exceed the solubility limit of such biocide in the solvent or solvent system. The biocide type that useful in the present method is one that is not only substantially insoluble in water but also forms elongated crystals, such as 3-iodo-2-propynyl-butylcarbamate (IPBC), which comprises a preferred embodiment of the invention. In preferred embodiment the aqueous system is a recirculating aqueous system, and more preferably is a recirculating cooling tower system. The invention and its other preferred embodiments are discussed in more detail below.

PREFERRED EMBODIMENTS OF THE INVENTION

As demonstrated in the Examples hereof, the present invention provides a method wherein wood surfaces treated thereby provides a high degree of resistance to the growth of algae and algae-like microorganisms when subjected to conditions thereafter that simulate, or are more severe than, conditions encountered at the site of the deck of a recirculating cooling tower, and further that such resistance continues for a significant period of time. While a chemical such as IPBC is more expensive on a per pound basis than chlorine, the direct treatment of the wood surface in such a manner that resistance to algae growth continues for a significant period of time renders the present method extremely cost effective when compared to any treatment of the bulk water. Further the duration of the effectiveness of the treatment should greatly extend the time intervals between shut-down of the aqueous system to scrub the algae growth off the wood surface(s). In addition, since the amount of biocide being used to treat the wood surface is insignificant in comparison to the amount of bulk water employed typically in such aqueous systems, any leachate therefrom is likewise insignificant, and contamination of the bulk water is removed as a consideration.

As mentioned above, the steps of application of the biocide in a suitable solvent, and then the flooding of the wood surface so treated, are successive steps by which it is believed that sufficient entrapment of the biocide within the wood cavities and fibers ensues to provide the degree and endurance of algae control provided by the present invention. As a practicality, such steps generally would be preceded by the isolation of the wood surface to be treated from the aqueous system for the purpose of enabling the treatment steps to be conducted, and further followed by the step of recontacting the treated wood surface with the waters of the aqueous system, which recontacting step may be, but need not be, the above-noted flooding with water step of the present invention. In other words, for instance with a deck of a cooling tower, the tower may be shut down and the wood surfaces of the deck scrubbed to remove algae growth, and then biocide in suitable solvent applied, followed by the recommencement of the operation of the cooling tower, which generally would be well sufficient to flood the wood surface with sufficient water so as to exceed the solubility limit of such biocide in the solvent or solvent system. One can of course undertake a flooding step with water other than the water of the aqueous system.

As mentioned above, a suitable biocide is one that is substantially insoluble in water. By the phrase "substantially insoluble in water" is meant sufficiently insoluble so that a practical amount of the biocide is thrown out of solution upon flooding. Given the relatively small amount of biocide being utilized by virtue of the application at the site of the wood surfaces, in comparison to the vast amount of water normally employed in aqueous systems, particularly industrial aqueous systems, an otherwise suitable biocide that is more water soluble than IPBC would not unduly burden the economics of the method. IPBC is soluble to the extent of about 188 ppm at 25° C. in water.

The characteristic of being substantially insoluble in water alone is insufficient for a suitable biocide for the present invention. The biocides employed in the comparate examples of Examples 1 and 2 below are water-insoluble biocides that are therein shown to lack the degree and endurance of the present invention although applied in the same manner. A suitable biocide must also form elongated crystals, or long water-soluble crystalline needles, as does IPBC. Of course a suitable biocide must also provide biocide activity against algae and algae-like microorganisms when utilized according to the method of the present invention, as does IPBC.

In preferred embodiment, particularly with respect to the preferred embodiment utilizing IPBC as the active agent, the biocide is applied to the wood as a solution in a solvent, which solvent includes a water miscible organic solvent. For IPBC any water-miscible polar solvent should be sufficient, such as butylcarbitol, or a mixture of such polar solvent and water of suitable composition to solubilize the biocide. In preferred embodiment, the solution containing the biocide is held in contact with the wood surfaces being treated for a time period of from about 15 to about 120 minutes. As mentioned above, it is believed that the active agent is carried by the solvent or solvent system to, and into, the wood cavities and lumen of the tracheids, and hence such soaking for a period of time is preferred.

In further preferred embodiment the wood being treated is wet, and more preferably substantially saturated with water, at the time the active agent is applied to its surfaces. It is believed that when the wood is sufficiently water-saturated so that its cavities are moist or wet rather than dry, the active agent is more efficiently taken into and/or held within such cavities. In certain application, for instance the treatment of cooling tower decks, the wood is normally saturated with water and generally would not be dried out prior to treatment.

In the following Examples 1 and 2, besides the preparation of the wood slats described therein, the slats were all placed in water, which was then heated to the boiling point, and then the slats were allowed to drain. This was done before the growth of algae on the slats. This provided a degree of water saturation simulating that of a cooling tower deck.

The Algae Test Units

The Algae Test Units utilized in Example 1 and 2 below are recirculating water systems that simulate recirculating cooling towers on a laboratory scale for testing algae control at the site of the deck. These Units are comprised of a water reservoir above which is disposed a plastic holder or deck, on top of which is placed the wooden test specimens or slats, and above that is a cool fluorescent light fixture that provides from 500-700 foot candles of light at the surface of the test specimens when in place. The Units are provided with a water pump and the water (generally about 4 liters) recirculates from the reservoir over the slats on the deck. The Units are constructed of plastic, and are open to the air.

The Rating System

The rating system for determination of the degree of resistance to algae growth used for the tests of Examples 1 and 2 below is as follows. "Excellent resistance" is no algae growth observable on the test specimen or slat. "None" is the presence of algae, several millimeters thick, over the entire test slat. Midway between these extremes is the rating of "good", which is algae growth in the amount of about 50 percent that of "no resistance" or "none" rating. Similarly, a "very good" rating is for the presence of algae growth in the amount of 25 percent that of a "no resistance" rating, and a "fair" rating is for the presence of algae growth in the amount of 75 percent of a "none" or "no resistance" rating. Where duplicate test specimens (slats) are used, a single rating is indicative of the same degree of algae growth being present on both slats.

The Algae

The term "algae" as used in all instances in Examples 1 and 2 below refers to the Oscillatoria species, which is very prevalent in algae growths on cooling tower decks. This species is generally considered a blue-green algae, and has been recently classified as a cyanobacteria.

The terms "algae" and "algae and algae-like microorganisms" as used herein generally both include the Oscillatoria species and other similar algae-like species.

EXAMPLE 1

Six leached bass wood slats (34 mm × 120 mm) with heavy algae growth were prepared by dragging the edge of a single edge razor blade against the surfaces to bare (clean) the surfaces of algae while not cutting or removing any wood. Upon such cleaning, the surfaces of the slats all had a green discoloration from embedded algae growth which served as the primary source of algae contamination in this test. This preparation of the slats simulated actual clean-up or scrubbing conditions used on open deck recirculating towers to remove algae growth. The surfaces of two of the slats were flooded for sixty minutes with a 1.0 weight percent solution of IPBC in butyl carbitol (25.0 weight percent) and deionized water (74.0 weight percent), after which they were drained on paper towelling, without blotting or wiping, and placed on the top deck of a first Algae Test Unit. As a comparative example, two of the other prepared slats were treated as described above for the IPBC treated slats with a 1.0 weight percent alkylphosphate derivative in butyl carbitol (25 weight percent) and deionized water (74.0 weight percent), and after draining, as described above, placed on the top deck of a second Algae Test Unit. As a blank, the last two prepared slats were treated, as described above, with 25 weight percent butyl carbitol in deionized water, and placed on the top deck, after draining, of a third Algae Test Unit. The water used in all of the test units was comprised of:

| | | |
|---|---|---|
| a. ammonium sulfate | 1.0 | gram |
| b. magnesium sulfate (MgSO$_4$.7H$_2$O) | 1.0 | gram |
| c. sodium tripolyphosphate | 1.0 | gram |
| d. sodium chloride | 1.0 | gram |
| e. ferric citrate (5%) | 0.5 | ml. |
| f. deionized water | 4.0 | liters |

This water composition, containing algae nutrients, provided a degree of acceleration to the test. In addition the cool fluorescent light sources of the Algae Test Units were employed continuously (24 hours per day) to further accelerate the test. The water of the Algae Test Units was changed, again using the composition set forth above, after the first 48 hours and thereafter once per week. All of the slats were examined at intervals and judged as to the degree of control (algae growth resistance) shown at that point in time, using the rating system described above. The results of such examinations and ratings are set forth below in Table I.

TABLE I

| | Degree of Resistance | | |
|---|---|---|---|
| Time Interval (days from start) | IPBC Treated Slats | Comparative Example | Blank |
| 3 days | excellent | excellent | none |
| 11 days | excellent | good | none |
| 16 days | excellent | fair | none |
| 22 days | very good to excellent | poor | none |
| 30 days | very good | none | none |
| 86 days | good to very good | none | none |
| 101 days | good | none | none |
| 141 days | good to fair | none | none |

EXAMPLE 2

The test described in Example 1 was repeated with the following changes. Again six slats were prepared by baring the wood, two of which were treated with the IPBC solution as described in Example 1, and the other two with a commercial microbiocide containing 10 weight percent tributyltinoxide. These two sets of slats (example and comparative example) were placed in separate Algae Test Units, each together with one untreated slat from which the algae growth was removed. The untreated slats were placed between the treated slats. After 48 hours from the start of of the tests both Algae Test Units were disassembled, washed, reassembled and, with the slats in place, purged three times with two hours of recirculating clean deionized water to remove any chemical leachates, and hence avoid any algae control effect therefrom. Then to each Algae Test Unit was added, directly before the deck, a slat containing heavy algae growth to provide an additional contamination source, and the Units were placed on-stream again. Further after 11 and 14 days 10 ml. of algae inoculum were added to both Units. The algae inoculum was prepared by osterizing 5 gm. of algae (wet wet) in 30 ml. of deionized water for 10 to 15 seconds at high speed until all of the algae was fragmented. Again, all other test parameters and methods were as described above in Example 1. The results of the periodic examinations and ratings are set forth below in Table II.

TABLE II

| | Degree of Resistance | |
|---|---|---|
| Time Interval (days from start) | Example | Comparative Example |
| 36 days | excellent | excellent |
| 49 days | excellent | very good |
| 56 days | excellent | none |
| 72 days | excellent | none |
| 87 days | good | none |
| 127 days | good to fair | none |

INDUSTRIAL APPLICABILITY OF THE INVENTION

The present invention is applicable to those industries in which fouling due to at least in part microbial growth is a problem, including without limitation cooling tower systems.

I claim:

1. A method of controlling growth of algae and algae-like microorganisms on a surface of wood that is normally in contact with water of an aqueous system by imparting to said surface of wood resistance to growth of algae and algae-like microorganisms which persists while said surface of wood is in substantially continuous contact with said water of said aqueous system, comprising:

substantially isolating said surface of wood from said water of said aqueous system and while said surface of wood is so isolated applying to said surface of wood a solution of 3-iodo-2-propynylbutylcarbamate, said solution containing at least about 0.1 weight percent of said 3-iodo-2-propynylbutylcarbamate in a solvent system that contains water and a water-miscible organic solvent for said 3-iodo-2-propynylbutylcarbamate in sufficient amount to render said 3-iodo-2-propynylbutylcarbamate soluble in said solvent system; and then flooding said surface of wood with sufficient water to exceed the solubility limit of the 3-iodo-2-propynylbutylcarbamate in said solvent system and bringing said surface of wood into substantially continuous contact with said water of said aqueous system for at least a substantial time period.

2. The method of claim 1 wherein said water-miscible organic solvent is butylcarbitol.

3. The method of claim 1 wherein said solution of 3-iodo-2-propynylbutylcarbamate is applied to said surface of wood by soaking said surface of wood for a time period of from 15 to 120 minutes.

4. The method of claim 1 wherein said wood being treated is at least moist.

5. A method of controlling growth of algae and algae-like microorganisms on a wood surface of a recirculating aqueous system which is normally in substantially continuous contact with recirculating waters of said recirculating aqueous system by treating said wood surface to impart a resistance to growth of algae and algae-like microorganisms which persists while said wood surface is un substantially continuous contact with said recirculating waters comprising:

substantially isolating said wood surface from said recirculating waters of said recirculating aqueous system;

then removing the bulk of any algae and algae-like microorganisms from said wood surface;

then soaking said wood surface with a solution of 3-iodo-2-propynylbutylcarbamate, said solution containing at least about 0.1 weight percent of said 3-iodo-2-propynylbutylcarbamate in a solvent system that contains water and a water-miscible organic solvent for said 3-iodo-2-propynylbutylcarbamate in sufficient amount to render said 3-iodo-2-propynylbutylcarbamate soluble in said solvent system; and then flooding said wood surface, while said wood surface is soaked with said solution, with sufficient water to exceed the solubility limit of said 3-iodo-2-propynylbutylcarbamate in said solvent system and bringing said wood surface into substantially continuous contact with said recirculating waters.

6. The method of claim 5 wherein said water-miscible organic solvent is butylcarbitol.

7. The method of claim 5 wherein said recirculating aqueous system is a recirculating cooling tower.

8. The method of claim 7 wherein said wood surface is the surface of an open deck of said recirculating cooling tower.

9. The method of claim 8 wherein said solution contains from 0.1 to 10.0 weight percent of said 3-iodo-2-propynylbutylcarbamate.

10. The method of claim 9 wherein said wood surface is soaked with said solution for a time period of from 15 to 120 minutes before flooding with water.

11. The method of claim 10 wherein said time period is from 30 to 90 minutes.

12. A method for controlling growth of algae and algae-like microorganisms on a surface of wood which wood is normally in contact with water of an industrial aqueous system, comprising sequentially:

removing from said surface of said wood the bulk of any algae and algae-like microorganisms that are present;

then treating said wood, while said wood is saturated with, but not covered by, water, by applying to said surface of said wood a solution of a substantially water-insoluble, elongated-crystal forming biocide in a solvent system, said solvent system being comprised of water and a water-miscible polar organic solvent, said water-miscible polar organic solvent being present in said solvent system in sufficient amount to solubilize said biocide in said solvent system, for a time period of from 15 to 120 minutes; and then flooding said surface of said wood with sufficient water to exceed the solubility limit of said biocide in said solvent system, whereby resistance to the growth of algae and algae-like mirorganisms on said surface of said wood when in contact with said water of said industrial aqueous system is imparted to said wood.

* * * * *

UNITED STATES PATENT AND TRADEMARK OFFICE
CERTIFICATE OF CORRECTION

PATENT NO. : 4,915,909
DATED : Apr. 10, 1990
INVENTOR(S) : Peter Song

It is certified that error appears in the above-identified patent and that said Letters Patent is hereby corrected as shown below:

In Claim 5, column 6, line 62, delete "un" and substitute therefor -- in --.

Signed and Sealed this

Twelfth Day of March, 1991

Attest:

HARRY F. MANBECK, JR.

*Attesting Officer*     *Commissioner of Patents and Trademarks*